US012390659B2

(12) United States Patent
Lim

(10) Patent No.: US 12,390,659 B2
(45) Date of Patent: Aug. 19, 2025

(54) APPARATUS AND METHOD FOR PHOTOBIOMODULATION-BASED ALTERNATIVE TO ELECTRICAL VAGUS NERVE STIMULATION AND DEEP BRAIN STIMULATION RELATED TO MOVEMENT DISORDERS

(71) Applicant: Lew Lim, Toronto (CA)

(72) Inventor: Lew Lim, Toronto (CA)

( * ) Notice: Subject to any disclaimer, the term of this patent is extended or adjusted under 35 U.S.C. 154(b) by 339 days.

(21) Appl. No.: 17/776,174

(22) PCT Filed: Oct. 27, 2020

(86) PCT No.: PCT/IB2020/060064
§ 371 (c)(1),
(2) Date: May 11, 2022

(87) PCT Pub. No.: WO2021/094860
PCT Pub. Date: May 20, 2021

(65) Prior Publication Data
US 2022/0387819 A1    Dec. 8, 2022

Related U.S. Application Data

(60) Provisional application No. 62/934,024, filed on Nov. 12, 2019.

(51) Int. Cl.
*A61N 5/06*    (2006.01)
(52) U.S. Cl.
CPC .... *A61N 5/0622* (2013.01); *A61N 2005/0647* (2013.01); *A61N 2005/066* (2013.01); *A61N 2005/0663* (2013.01)

(58) Field of Classification Search
CPC ...... A61N 1/3756; A61N 1/056; A61N 1/362; A61N 1/378; A61N 2001/0578;
(Continued)

(56) References Cited

U.S. PATENT DOCUMENTS 11,813,476 B1 * 11/2023 Shanks ................ A61N 5/0622
2009/0149797 A1 * 6/2009 Dacey, Jr. ............. A61N 1/303
604/20
(Continued)

FOREIGN PATENT DOCUMENTS

WO    2016151377 A1    9/2016
WO    2019053625 A1    3/2019

OTHER PUBLICATIONS

International Search Report issued Feb. 1, 2021 in connection with PCT Application No. PCT/IB2020/060064, 4 pages.
(Continued)

*Primary Examiner* — Carl H Layno
*Assistant Examiner* — Manolis Pahakis
(74) *Attorney, Agent, or Firm* — Foley IP Law, PLLC

(57) ABSTRACT

A self-administrable apparatus for performing non-invasive neurostimulation therapy of a living mammal on-demand, said self-administrable non-invasive neurostimulation apparatus comprising: one or more configured irradiation units comprising a portable hollow casing having fixed dimensions, a sized internal spatial volume and an external surface configuration suitable for application to a body, and a controller assembly able to control on-demand delivery of light energy from said configured irradiation units into an interior part of the body in-vivo.

16 Claims, 10 Drawing Sheets

(58) Field of Classification Search
CPC ..... A61B 17/3468; A61B 2017/00477; A61M 25/0082; A61M 25/0136
See application file for complete search history.

(56) References Cited

U.S. PATENT DOCUMENTS

| | | | | |
|---|---|---|---|---|
| 2015/0283265 | A1* | 10/2015 | Peyman | A61K 45/06 424/491 |
| 2016/0287898 | A1* | 10/2016 | Smith | A61N 5/0622 |
| 2016/0375265 | A1* | 12/2016 | Kim | A61N 5/0613 607/89 |
| 2018/0015301 | A1* | 1/2018 | Lim | A61N 5/0622 |
| 2019/0321651 | A1* | 10/2019 | Deisseroth | A61K 48/0083 |
| 2020/0046968 | A1* | 2/2020 | Herr | A61K 9/0009 |
| 2020/0094054 | A1* | 3/2020 | Sharma | A61N 1/36034 |
| 2020/0206526 | A1* | 7/2020 | Kim | A61N 5/0622 |
| 2020/0261722 | A1* | 8/2020 | Alataris | A61N 5/0603 |
| 2021/0346715 | A1* | 11/2021 | Shanks | A61N 5/0622 |
| 2022/0054841 | A1* | 2/2022 | Doguet | A61N 5/0622 |

OTHER PUBLICATIONS

Written Opinion issued Feb. 1, 2021 in connection with PCT Application No. PCT/IB2020/060064, 6 pages.

* cited by examiner

APPARATUS AND METHOD FOR PHOTOBIOMODULATION-BASED ALTERNATIVE TO ELECTRICAL VAGUS NERVE STIMULATION AND DEEP BRAIN STIMULATION RELATED TO MOVEMENT DISORDERS

CROSS REFERENCE TO RELATED APPLICATIONS

The present application is a 35 U.S.C. § 371 national stage entry of PCT/IB2020/060064, which has an international filing date of Oct. 27, 2020 and claims priority to U.S. Provisional Patent Application No. 62/934,024, filed on Nov. 12, 2019.

FIELD OF THE INVENTION

The present invention relates to neurostimulation, and more specifically, to an apparatus and method for neurostimulation using photobiomodulation.

BACKGROUND ART

Photobiomodulation (PBM)

Photobiomodulation (PBM), also known as low-level light therapy (LLLT), is a biostimulation technique that has shown promise in treating a number of conditions, including dementia and Alzheimer's Disease.

The biochemical mechanism of PBM interaction can be classified into direct and indirect effects. The direct effects include increasing the activity of ion channels such as the Na+/K+ ATPase and the indirect effects include regulating important secondary messengers such as calcium, cyclic adenosine monophosphate (cAMP) and reactive oxygen species (ROS)—all of which result in diverse biological cascades. These biological cascades lead to effects such as the maintenance of homeostasis and activating protective, anti-oxidant and proliferative gene factors, as well as the systematic responses, such as cerebral blood flow, which is deficient in neurocognitive disorders.

The most well investigated mechanism of action of PBM is its fundamental effect on mitochondrial function. PBM has been demonstrated to increase the activity of complexes in the electron transport chain of mitochondria, comprising complex I, II, III, IV and succinate dehydrogenase. In complex IV, the enzyme cytochrome c oxidase (CCO), functions as photo acceptor as well as transducer. CCO specifically accepts and transduces light in the red (620-700 nm) and the near-infrared (780-1110 nm) spectrums, wavelengths of lights which can be processed in PBM. The process increases the amount of ATP produced, as well as cyclic adenosine monophosphate (cAMP) and reactive oxygen species (ROS). The increase in ATP increases the activity of ion channels regulating cAMP and calcium, which results in the stimulation of diverse biological cascades and activate up to 110 genes for transcription, which lead to healing and recovery activities and the prolongation of the production of energy by the mitochondria. One of the most prominent responses to PBM is the activation of sodium pumps and the Na+/K+ ATPase, which leads to greater membrane stability and resistance to depolarization.

In addition to increasing levels of ATP and cAMP, it has been observed that PBM results in an increase in nitric oxide (NO) levels, dissociated from CCO when photons are absorbed by CCO. The dissociation of NO from CCO leads to the enhancement of ATP production and acts as a vasodilator as well as a dilator of lymphatic flow, and can signal to activate a number of beneficial cellular pathways.

Vagus Nerve Stimulation (VNS)

The vagus nerve is the tenth cranial nerve and arises from the medulla. It carries both afferent and efferent fibers. The afferent vagal fibers connect to the nucleus of the solitary tract, which in turn projects connections to other locations in the central nervous system.

Vagus Nerve Stimulation (VNS) is a fairly well recognized treatment method that focuses on the tenth cranial nerve that connects the gut-brain nervous circuit. A variety of health conditions are dependent on this circuit, and many are related to brain functions. Regulatory-cleared treatments include intractable epilepsy and treatment-resistant depression. There is also some literature based on clinical studies to use VSN in the treatment of drug addiction, Chrohn's disease, inflammatory bowel diseases (IBD), fibromyalgia, cluster headaches, pulmonary disease, heart disease, traumatic brain injury, diabetes, rheumatoid arthritis, post-traumatic stress disorder (PTSD) and anxiety.

The device currently used for VNS mainly consists of a generator the size of a matchbox that is implanted under the skin below the person's collarbone. Lead wires from the generator are tunneled up to the patient's neck and wrapped around the left vagus nerve at the carotid sheath, where it delivers electrical impulses to the nerve. Conventional locations for the placement of an electrode are on the neck closest to the vagus nerve and on the ear lobe. The "dose" administered by the currently used VNS device needs to be set, which is done via a magnetic wand. The parameters adjusted may include current, frequency, pulse width, and duty cycle.

There are also "wearable" devices for VNS. "Wearable" devices are being tested and developed that involve transcutaneous stimulation and do not require surgery. Electrical impulses are targeted at the aurical (ear), at points where branches of the vagus nerve have cutaneous representation. Such devices have been tested in clinical trials for the treatment of resistant major depressive disorder.

Deep Brain Stimulation (DBS) for Movement Disorders

Movement disorders are clinical syndromes with either an excess of movement or a paucity of voluntary and involuntary movements, unrelated to weakness or spasticity. They include Parkinson's disease, Tourette Syndrome, essential tremor, and dystonia. These disorders have been found to respond to deep brain stimulation (DBS) to various degrees.

DBS is a neurosurgical procedure involving the placement of a medical device, called a neurostimulator (sometimes referred to as a 'brain pacemaker'), which sends electrical impulses through implanted electrodes to specific targets in the brain (brain nuclei) for the treatment of movement disorders. While its underlying principles and mechanisms are not fully understood, DBS directly changes brain activity in a controlled manner.

DBS has been approved by the Food and Drug Administration as a treatment for essential tremor and Parkinson's disease since 1997. DBS was approved for dystonia in 2003, obsessive-compulsive disorder in 2009, and epilepsy in 2018. DBS has been studied in clinical trials as a potential treatment for chronic pain for various affective disorders.

Parkinson's Disease

For Parkinson's Disease (PD), DBS is used to manage some of the symptoms that cannot be adequately controlled with medications. It is recommended for people who have PD with motor fluctuations and tremor inadequately controlled by medication, or to those who are intolerant to medication, as long as they do not have severe neuropsychiatric problems. Generally, DBS is associated with 30-60% improvement in motor score evaluations.

In addition, in PD DBS, most surgeons prefer bilateral stimulation although there are cases with profound unilateral symptoms that do better with a unilateral approach.

There is no one treatment that fits all PD patients. Determining the optimum target area and the decision on unilateral or bilateral placements is an arduous and costly process. If there is a non-invasive low-cost alternative, it would be beneficial.

SUMMARY OF THE INVENTION

In one aspect, the present invention provides a self-administrable apparatus for performing non-invasive neurostimulation therapy of a living mammal on-demand, said self-administrable non-invasive neurostimulation apparatus comprising:
one or more configured irradiation units comprising a portable hollow casing having fixed dimensions, a sized internal spatial volume and an external surface configuration suitable for application to a body, said portable hollow casing of each configured irradiation unit being comprised of:
(i) a light energy transmitting material which forms at least a portion of the configured external surface for said hollow casing of each configured irradiation unit; and
(ii) at least one light generating unit housed and contained within said internal spatial volume of said hollow casing of each configured irradiation unit and which is capable of generating light energy of at least one preselected wavelength selected from the group consisting of near infrared light wavelengths and visible red light wavelengths, at a predetermined energy intensity and for a preset time duration on-demand sufficient to penetrate through skin and to pass into an interior part of the body,
whereby said configured irradiation units can emit light energy after application to the body and achieve passage of said emitted light energy through the skin into an interior part of the body in-vivo;
a frame adapted for support of said configured irradiation units and for at will placement of said light transmitting external surface of said configured irradiation units at a fixed position and desired irradiation direction;
a controller assembly able to control on-demand delivery of light energy from said configured irradiation units into an interior part of the body in-vivo, said controller assembly including:
(a) a power source of on-demand direct electrical current,
(b) a central processing unit for controlling and directing the flow of such direct electrical current,
(c) at least one connector in electrical communication with the power source for on-demand conveyance of direct electrical current to the central processing unit, and
(d) at least one connector in electrical communication with the configured irradiation units for on-demand conveyance of direct electrical current from said central processing unit to said light generating units.

In another aspect, the present invention provides a self-administrable method for performing non-invasive neurostimulation therapy of a living mammalian subject on-demand, said self-administrable non-invasive neurostimulation method comprising the steps of:

(A) obtaining a light energy-emitting apparatus comprised of:
one or more configured irradiation units comprising a portable hollow casing having fixed dimensions, a sized internal spatial volume and an external surface configuration suitable for application to a body, said portable hollow casing of each configured irradiation unit being comprised of:
(i) a light energy transmitting material which forms at least a portion of the configured external surface for said hollow casing of each configured irradiation unit; and
(ii) at least one light generating unit housed and contained within said internal spatial volume of said hollow casing of each configured irradiation unit and which is capable of generating light energy of at least one preselected wavelength selected from the group consisting of near infrared light wavelengths and visible red light wavelengths, at a predetermined energy intensity and for a preset time duration on-demand sufficient to penetrate through skin and to pass into an interior part of the body,
whereby said configured irradiation units can emit light energy after application to the body and achieve passage of said emitted light energy through the skin into an interior part of the body in-vivo;
a frame adapted for support of said configured irradiation units and for at will placement of said light transmitting external surface of said configured irradiation units at a fixed position and desired irradiation direction;
a controller assembly able to control on-demand delivery of light energy from said configured irradiation units into an interior part of the body in-vivo, said controller assembly including:
(a) a portable and replenishable power source of on-demand direct electrical current,
(b) a central processing unit for controlling and directing the flow of such direct electrical current,
(c) at least one connector in electrical communication with the power source for on-demand conveyance of direct electrical current to the central processing unit, and
(d) at least one connector in electrical communication with the configured irradiation units for on-demand conveyance of direct electrical current from said central processing unit to said light generating units; and
(B) causing said light generating units of said one or more configured irradiation units to generate light energy of at least one preselected wavelength selected from the group consisting of near infrared light wavelengths and visible red light wavelengths, at a predetermined energy intensity and for a preset time duration on-demand sufficient to penetrate through the subject's skin and to pass into the interior of the subject's body.

DESCRIPTION OF THE DRAWINGS

The present invention may be better understood and more readily appreciated when taken in conjunction with the accompanying drawings, in which.

DESCRIPTION OF PREFERRED EMBODIMENTS OF THE INVENTION

Figure 1:
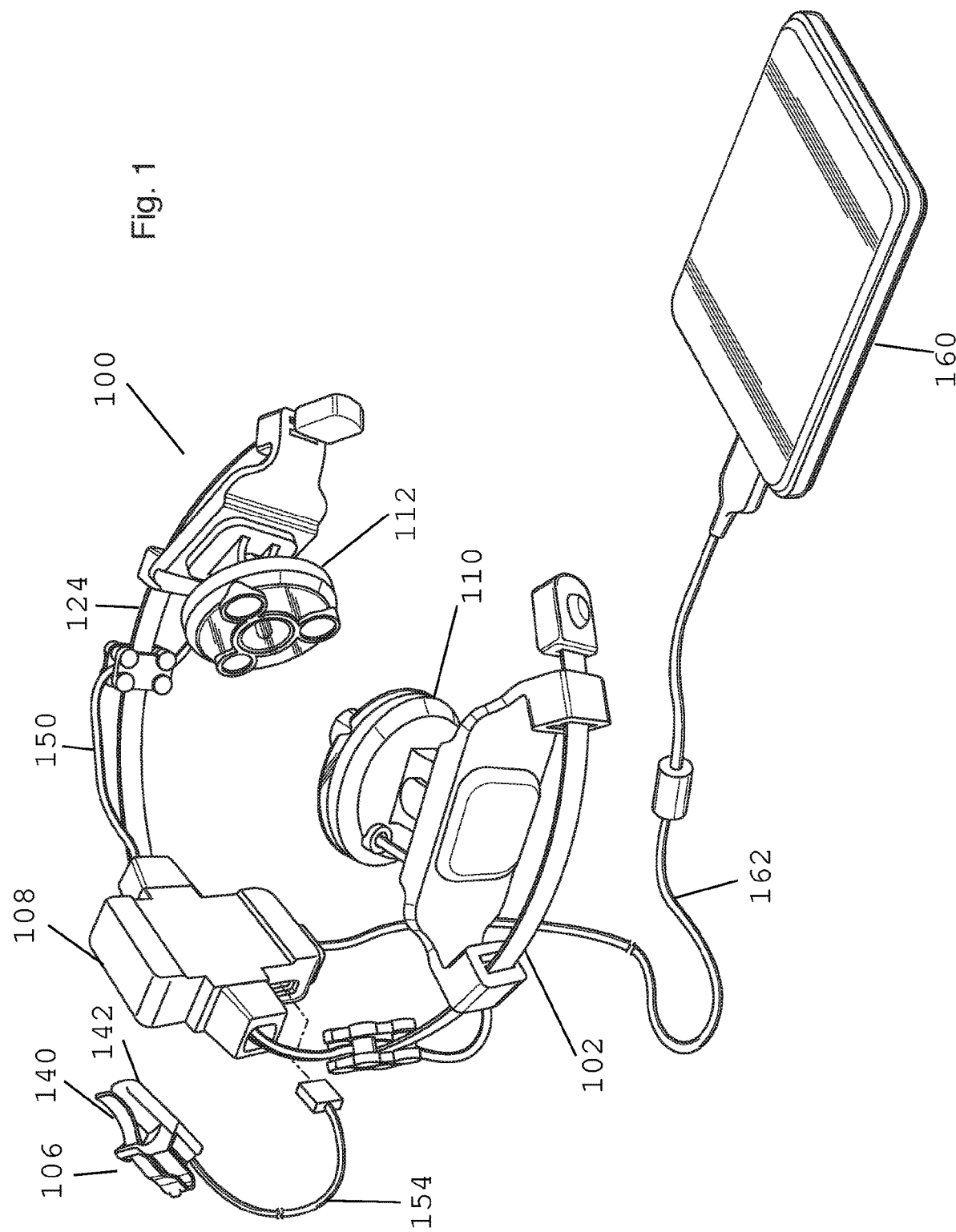
FIG. 1 illustrates a perspective view of a preferred embodiment of the apparatus of the present invention including optional elements of an intranasal unit and a power bank.
Figure 2:
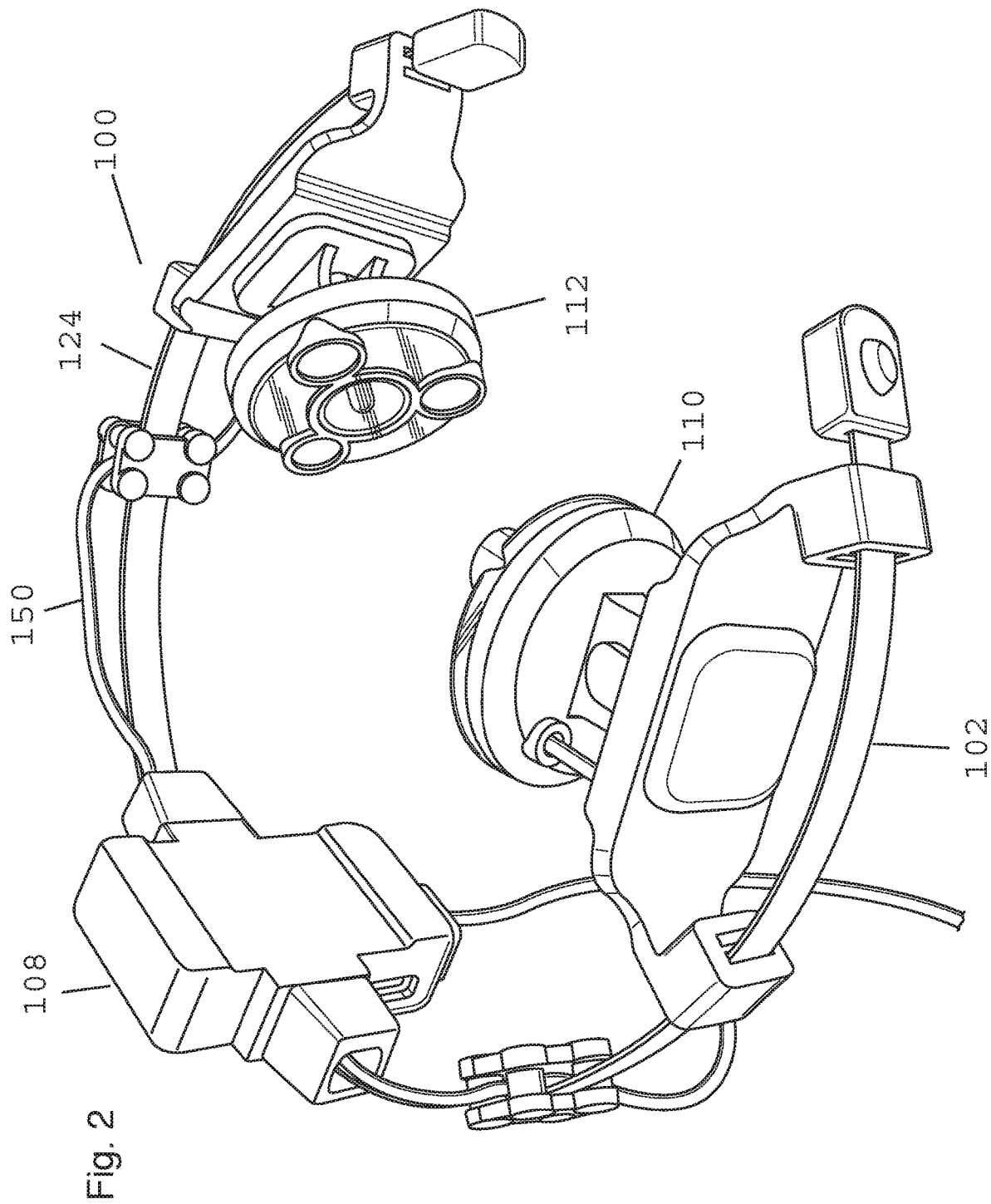
FIG. 2 illustrates a perspective view of a preferred embodiment of the apparatus of the present invention.

Photobiomodulation has been shown to have an effect on the central nervous system (CNS). PBM has also been shown to induce nerve cell activation that leads to repair. The evidence has been more pronounced on injured nerve cells but there has also been demonstrated stimulatory action on gene transcription factors to enable repair. At relatively high power densities, they have anti-inflammatory and analgesic properties.

Studies have shown that the brain (and central nervous system (CNS)) respond to PBM inducement in consistent and specific ways. For example, when gamma waves at around 40 Hz are used, the investigators observed that the faster brain oscillations, alpha (8-12 Hz), beta (12-30 Hz) and gamma (30-70 Hz), have increased power spectrum, whereas the slow waves, delta (0.5-4 Hz) and theta (4-8 Hz), have reduced power spectrum.

Components of the Preferred System/Apparatus

The system and apparatus of the present invention preferably comprises at least the following component parts:
(1) a portable hollow casing;
(2) one or more light generating units which are housed and contained within the interior spatial volume of the hollow casing;
(3) a source of electrical current;
(4) a process controller assembly; and
(5) optionally, a smart phone, tablet computer or other computing device.

These components may preferably be electrically linked together by at least one connector for transfer of direct electrical current from the source of electrical current to the controller assembly, and at least one connector for conveyance of direct electrical current from the controller assembly to the light generating unit.

1. Portable Hollow Casing

The present invention includes at least one portable hollow casing having fixed dimensions, a sized internal spatial volume and an external surface configuration suitable for application to the subject. The intended purposes and goals of the portable casing are twofold: (i) to serve as a containment chamber that is configured for easy application to the subject; and (ii) to act as a molded lens that reflects and directs emitted light waves to the subject.

Preferably, the portable casing may be constructed and formed of a light transmitting material over at least a portion of its external surface, and will encompass that volumetric zone intended for housing and containment of at least one light generating unit. By definition, such light transmitting material includes and encompasses transparent, translucent and opaque matter. However, in most instances, a completely clear and transparent matter is preferred.

2. Light Generating Unit(s)

The light generating unit will be able to deliver therapeutic light at wavelengths that include but are not necessarily limited to the following: (i) in the visible color spectral ranges, the visible red light wavelengths ranging between about 620-780 nm; and (ii) in the non-visible spectral ranges, the near-infrared light wavelengths ranging between about 780-1400 nm. In addition, the generated light energy waves and particles may alternatively be: (i) either coherent (as in lasers) or non-coherent (as in non-laser light emitting diodes (LEDs); (ii) be either pulsing or non-pulsing (continuous wave) in delivery; (iii) be either constant or non-constant in intensity; (iv) be either uniform or non-uniform in phase; (v) polarized and non-polarized; and (vi) have a regular or irregular flux.

Any conventionally known means for generating electromagnetic radiation or articles for propagating radiant energy are acceptable for use in the present apparatus. In the majority of embodiments, it is intended and expected that either a low level laser unit or a LED will be employed as the light generating unit(s) for irradiating purposes.

3. Source of Electric Current

It is preferred that a portable and replenishable source of on-demand direct electrical current exist as a component part of the apparatus and system of the present invention. The therapeutic treatment system and method provided by the instant invention is intended to deliver a specific energy dosage (measured in Joules), which is a function of power (in wattage) and time (in seconds), and which is deemed to be efficacious for each therapeutic treatment.

The power supply typically will convey energy in the form of direct electric current. Adequate quantities of electric current can be repeatedly conveyed from, for example, a single battery source or from a combination of several dry cells joined together in series or parallel. In some other desirable embodiments, the source of electric power will be in the form of a rechargeable power bank, a direct current battery unit (rechargeable from ordinary household alternating current receptacles) or as alternating current (AC) via a power adaptor. It is expected and intended that there will be several alternative embodiments with different combinations of these components and which would be suitable for different configurations of power, energy dosage and treatment time.

As to positioning, in some preferred embodiments, the power source is a discrete entity which is held and contained entirely within the internal confines of the controller assembly. In other preferred embodiments, however, the source of electric current can be a self-contained, separate and free standing unit which is in electrical communication with the controller assembly via an electrical cable and connector module linkage, such as a portable and rechargeable power bank. In an alternative embodiment, the source of electrical current is obtained by plugging the system and apparatus into the local electrical grid via a power adaptor.

4. Process Controller Assembly

The process controller assembly is a component having at least three structural features:
  (i) A receiving circuit for receipt of such electrical current as is transferred to the controller assembly from the electrical current source;
  (ii) A central processing unit (CPU) for controlling and directing the flow of such electrical current as is received by the controller assembly over time; and
  (iii) A delivery circuit for delivering direct electrical current from the controller assembly to the light generating unit(s).

It is intended and expected that the process controller assembly will be electrically linked to other essential components of the apparatus and thus typically will also have:
  (a) at least one connector for transfer of direct electrical current from the source of electrical current to the controller assembly; and
  (b) at least one connector for conveyance of direct electrical current from the controller assembly to the light generating unit(s).

These connectors typically are formed as insulated copper wire cables and jack modules that allow for quick and easy linkage and electrical communication with both the electrical current source and the light generating unit(s).

It is intended and expected that any conventionally known and interchangeable electric cables and connectors will be used to link the controller assembly to the irradiation lens. This also provides a distinct advantage and benefit to the user, namely the option to exchange one configured irradiation lens (able to transmit light at a first wavelength) for another irradiation lens (able to transmit light at a second and different wavelength), and thereby permits the use of different lasers and alternative light emitting diodes able to deliver different wavelengths of visible and invisible light energy with one single controller assembly.

In some preferred embodiments, the source of electrical current lies internally and is contained within the interior spatial volume of the controller assembly, and appears as an electric battery (dry cell or rechargeable unit). In this instance, the controller assembly also has a socket adapted for the attachment of an insulated copper wire cable and modular jack connector, whose other end is joined to the light generating unit disposed within the hollow casing.

The central processing unit ("CPU") of the controller assembly is preferably able to regulate light energy with respect to many different parameters including but not limited to: wavelength, coherency/synchrony, energy (Joules (J)), Power (Watts (W) or milliwatts (mW)) or irradiance (W/cm$^2$), radiant exposure (J/cm$^2$), exposure time (seconds), wave type (continuous or pulse), frequency (Hertz (Hz)), duty cycle (percentage), fraction protocol (number of patient treatment sessions), light beam size (area of landed beam), and light beam penetration (delivery) distance.

The process controller assembly will not operate in the absence of a source of electrical current. In addition, the controller assembly, besides preferably switching off the unit after a predetermined time, is a circuitry which provides power to drive the light generating unit(s) properly and efficiently. The controller also ensures that the power delivered to the light generating unit(s) is consistent. It therefore desirably monitors the battery strength where the source is a power bank or battery, and switches off the unit if the power bank or battery is unable to supply sufficient power to drive the circuitry properly.

5. Smart Phone, Tablet Computer or Other Computing Device

In one alternative embodiment, the function of the controller assembly may be replaced, in whole or in part, by smartphone, smartwatch, tablet computer, laptop computer, desktop computer or any appropriate computing device. The smart phone, for example, may operate on one of the more popular mobile platforms. The light generating unit(s) could be connected via a cable or wirelessly to the smart phone. The smart phone carries a downloadable software application that would largely duplicate the software functions in the controller assembly. A modified attachment containing interface processing software in a computer chip will provide an interface between the existing applicator and the proprietary smart phone platform. With this embodiment, the user need not carry an additional or separate controller unit, and yet the software application will also contain more software controls and graphic interfaces. Alternatives to the smart phone include a smartwatch, tablet computer, laptop computer, desktop computer or any appropriate computing device with the software application downloaded thereon.

In yet another alternative embodiment, the controller assembly works in combination with smartphone, smartwatch, tablet computer, laptop computer, desktop computer or any appropriate computing device. In particular, the computing device has downloaded thereon a software application which can: (i) turn the controller assembly on and off; and/or (ii) transmit instructions to the controller assembly to adjust the light energy parameters of each individual light generating unit, including but not limited to wavelength, coherency/synchrony, energy (Joules (J)), Power (Watts (W) or milliwatts (mW)) or irradiance (W/cm$^2$), radiant exposure or dose or fluence density (J/cm$^2$), exposure time (seconds), wave type (continuous or pulse), frequency (Hertz (Hz)), duty cycle (percentage), fraction protocol (number of patient treatment sessions), light beam size (area of landed beam), and light beam penetration (delivery) distance.

Furthermore, the computing device can serve as a system interface where a user enters instructions through the interface to turn the controller assembly on and off and/or adjust the light energy parameters of each individual light generating unit. Instructions may be entered by any known input component such as a touch screen, mouse, keypad, keyboard, microphone, camera or video camera. Once the user inputs instructions into the system interface, instructions are transmitted to the controller assembly which then adjusts the parameters of the light energy being delivered to by the light generating units.

In these embodiments, any conventionally known and interchangeable electric cables and connectors can be used to link the computing device to the controller assembly. Alternatively, the computing device may communicate with the controller assembly by wireless means. Connections between any of these components are implemented using appropriate wired or wireless communications via protocols such as BLUETOOTH™, Wi-Fi, Near Field Communications (NFC), Radio Frequency Identification (RFID), 3G, Long Term Evolution (LTE), Universal Serial Bus (USB) and other protocols and technologies known to those skilled in the art.

Preferred Embodiment for Vagus Nerve Stimulation (VNS)

Vagus nerve stimulation (VNS) is identified with the delivery of electrical pulses to the vagus nerve as the medium for stimulation. To date, there is no available VNS device that applies Photobiomodulation (PBM). The use of selected wavelength, dual-position delivery and pulse frequency are preferably part of how PBM is used for VNS in the present invention.

Present VNS devices which deliver electrical pulses are preferably set to pulse at about 10 to 30 Hz with various duty cycles. A PBM device that is positioned on similar locations of the body, pulsing at the same rate, with sufficient penetrative parameters, may produce similar or better outcomes.

The present VNS devices delivering electrical pulses usually produce an unpleasant side effect of mild electrical tingling. Unlike electrical stimulation used by the present VNS devices, light at the appropriate level of power and for the appropriate length of time gives a dose that is low enough not to produce any thermal sensation or other noticeable effect other than the presence of the device.

The present invention provides an apparatus for treating neurological conditions using PBM. It is a portable unit with the light emitting diode (LED) positioned on the neck closest to the vagus nerves. It is more convenient than delivering electrical pulses as lower power is used. Hence, there is the potential for greater portability through the use of rechargeable batteries, instead of having to extract power from the electrical wall sockets.

Preferred parameters may be a light wavelength of 810 nm, and LEDs having a power density between 25 and 100 mW/cm$^2$. However, wavelengths between 600 to 1500 nm are available options, as well as LED power of between 1 mW to 15 kW. Preferably, one practical (allowing for portability) and effective power density would be about 50 mW/cm$^2$. Preferred treatment times could range be 1 minute to 1 hour, but a preferred time is about 20 minutes.

Unlike conventional VNS devices, this system could have dual LED electrodes on both sides of the neck, with no side effects, and could still improve outcomes further. There is also no need for grounding the PBM system.

The form of the system could comprise of a controller with the appropriate electronic circuit driving the LED modules with the chosen parameters. The LED modules can be held together with a flexible steel band. The parameters can be controlled and determined by depressing physical buttons or icons on computer or smart phone apps. Readings and measures can also be displayed as images, text or numerical digits on the apps.

Preferred Embodiment for Deep Brain Stimulation (DBS) Related to Movement Disorders The apparatus and method of the present invention can also be used for Deep Brain Stimulation (DBS) in the treatment of movement disorders. In the present invention, instead of using electrodes to send electrical impulses as in the prior art, PBM is used.

In the treatment of Parkinson's Disease (PD), the apparatus of the present invention can be used to target the globus pallidus internus (GPi) and subthalamic nucleus (STN) for PBM. Treating one or both targets may be effective in improving motor symptoms. DBS of the STN allows greater medications, while DBS of the GPi has a direct anti-tremor effect and is preferred where there are cognitive and psychiatric symptoms. Other target areas for consideration are the posterior subthalamic area, the ventral intermediate nucleus of the thalamus and the pedunculopontine nucleus.

To irradiate the STN and GPi (which are close together), the light source can be positioned on the temporal cortical area just above the ear. Under the electroencephalography (EEG) 10-20 system, these are bilaterally labelled as the T3/T4 placements.

Tourette's syndrome and essential tremors are two of other movement disorders which may be treated by the apparatus and method of the present invention.

In Tourette's syndrome, the apparatus of the present invention is placed to target the basal ganglia for DBS by using PBM.

Essential tremors are identified with a dysfunctional cerebellum, so that would be a target area for the apparatus of the present invention. Again, in the present invention, PBM is used instead of electrodes sending electrical impulses.

Other movement disorders may hypothetically be addressed by targeting the known cortical areas associated with the specific conditions.

Preferred Embodiment of the Apparatus of the Present Invention

As shown in FIGS. 1 to 6, the present invention provides a preferred embodiment of an apparatus 100 which comprises a light therapy unit 102 and an intranasal unit 106. The controller 108 can serve as a central processing unit for the light therapy unit 102 and intranasal unit 106.

Figure 3:
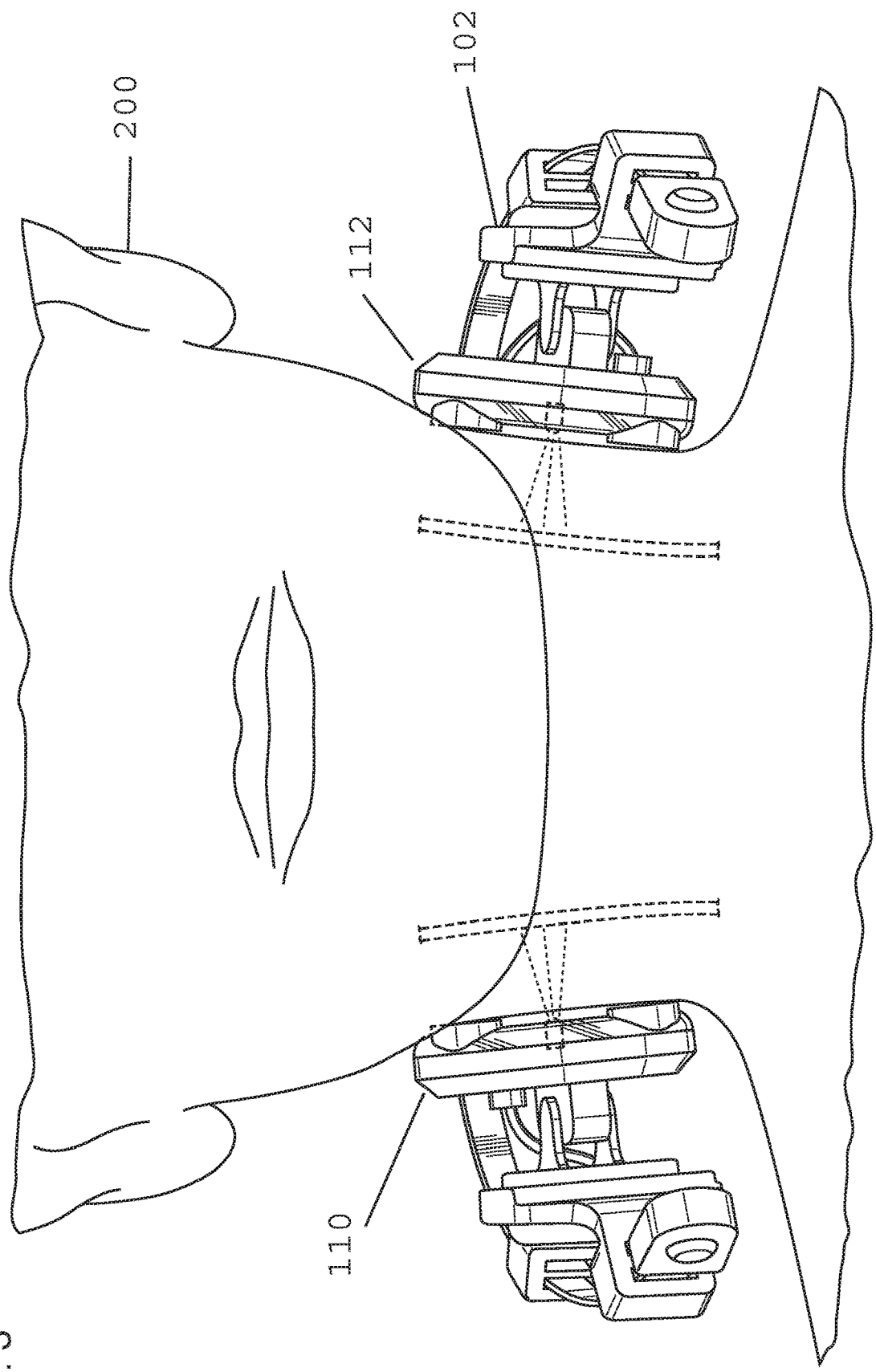
FIG. 3 illustrates a preferred embodiment of the apparatus of the present invention when about to be applied to a neck of a subject for Vagus Nerve Stimulation.
Figure 4:
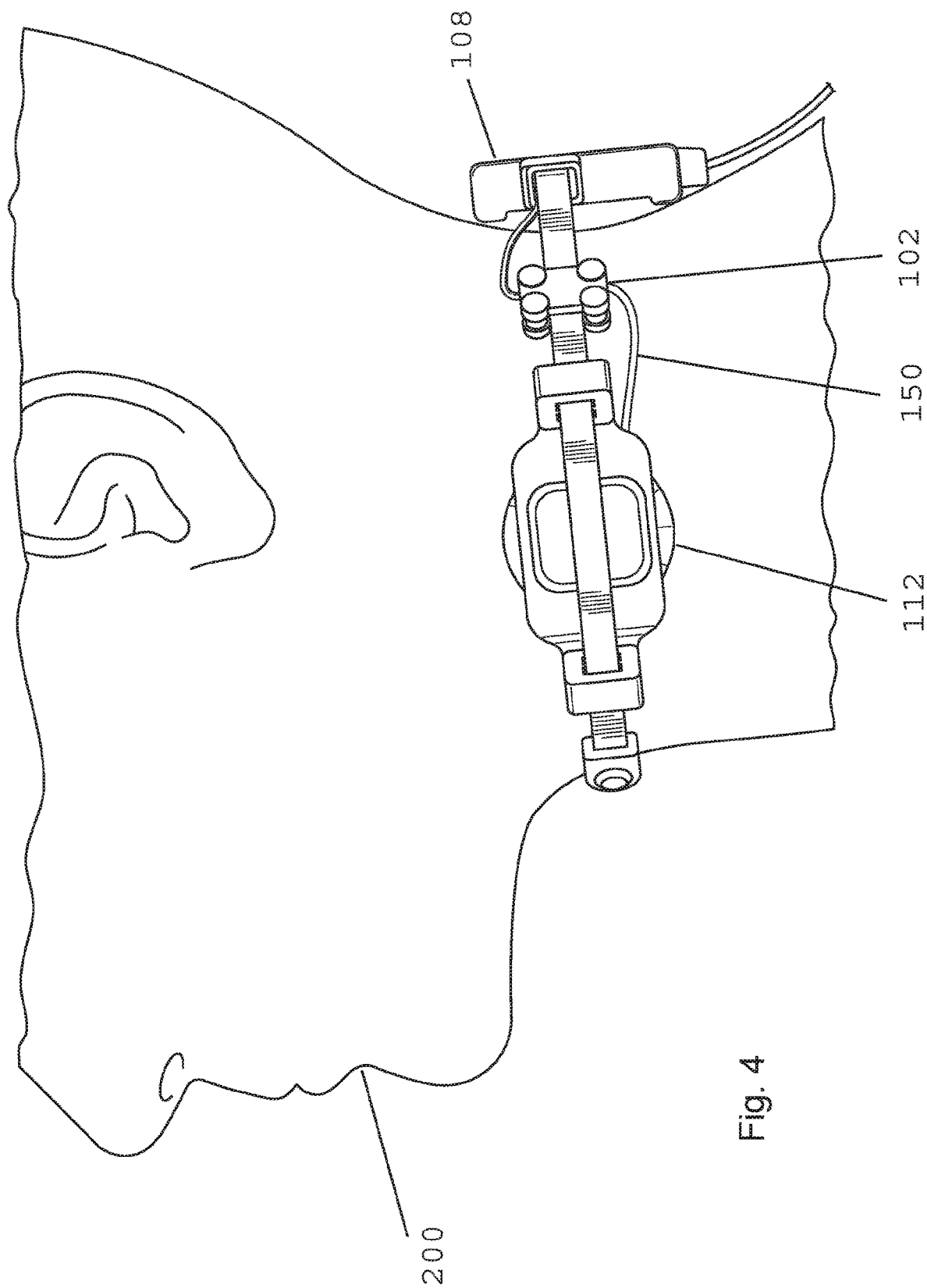
FIG. 4 illustrates a preferred embodiment of the apparatus of the present invention when applied to a neck of a subject for Vagus Nerve Stimulation.
Figure 5:
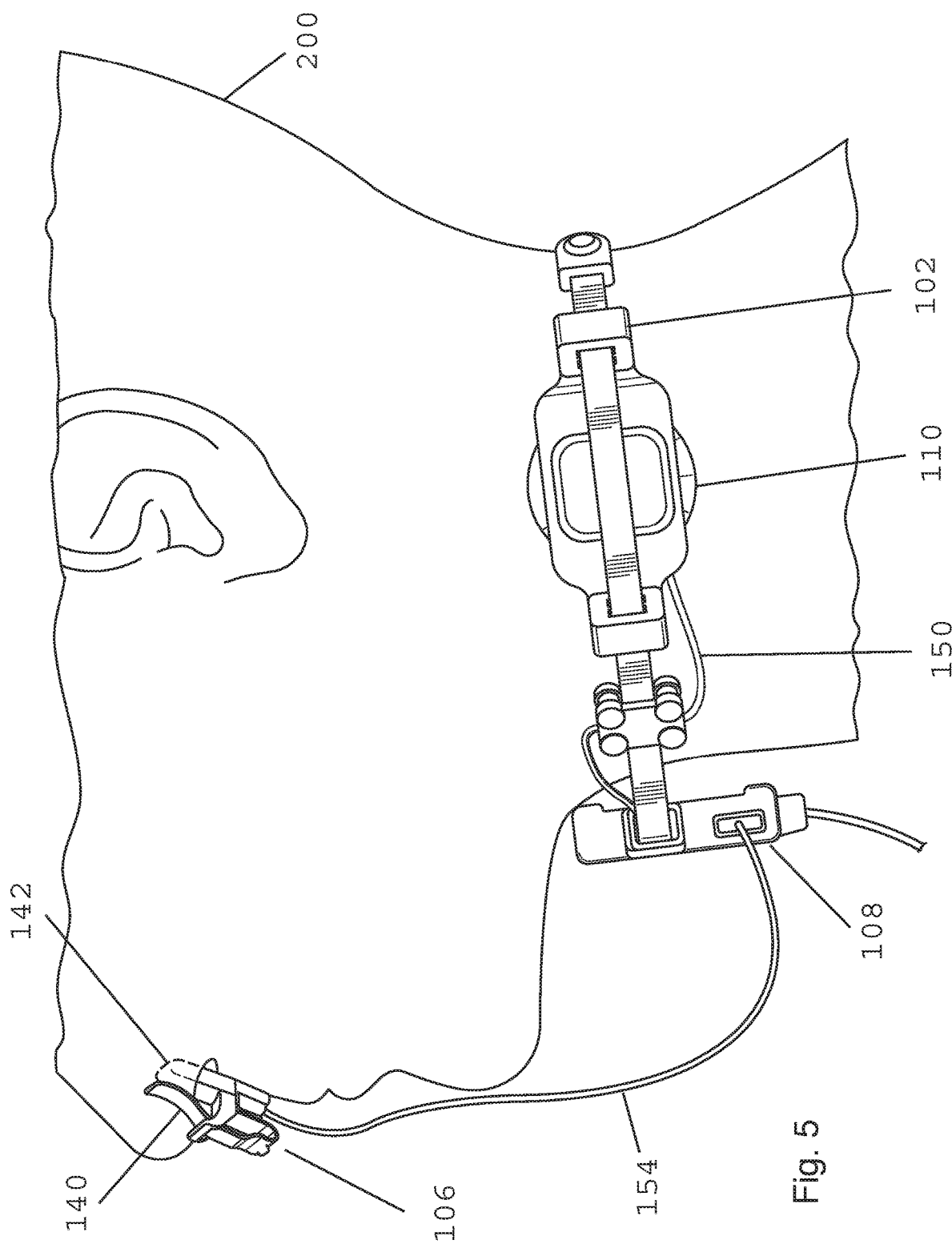
FIG. 5 illustrates a preferred embodiment of the apparatus of the present invention when applied to a neck of a subject for Vagus Nerve Stimulation, along with an optional intranasal unit applied to the nose of the subject.
Figure 6:
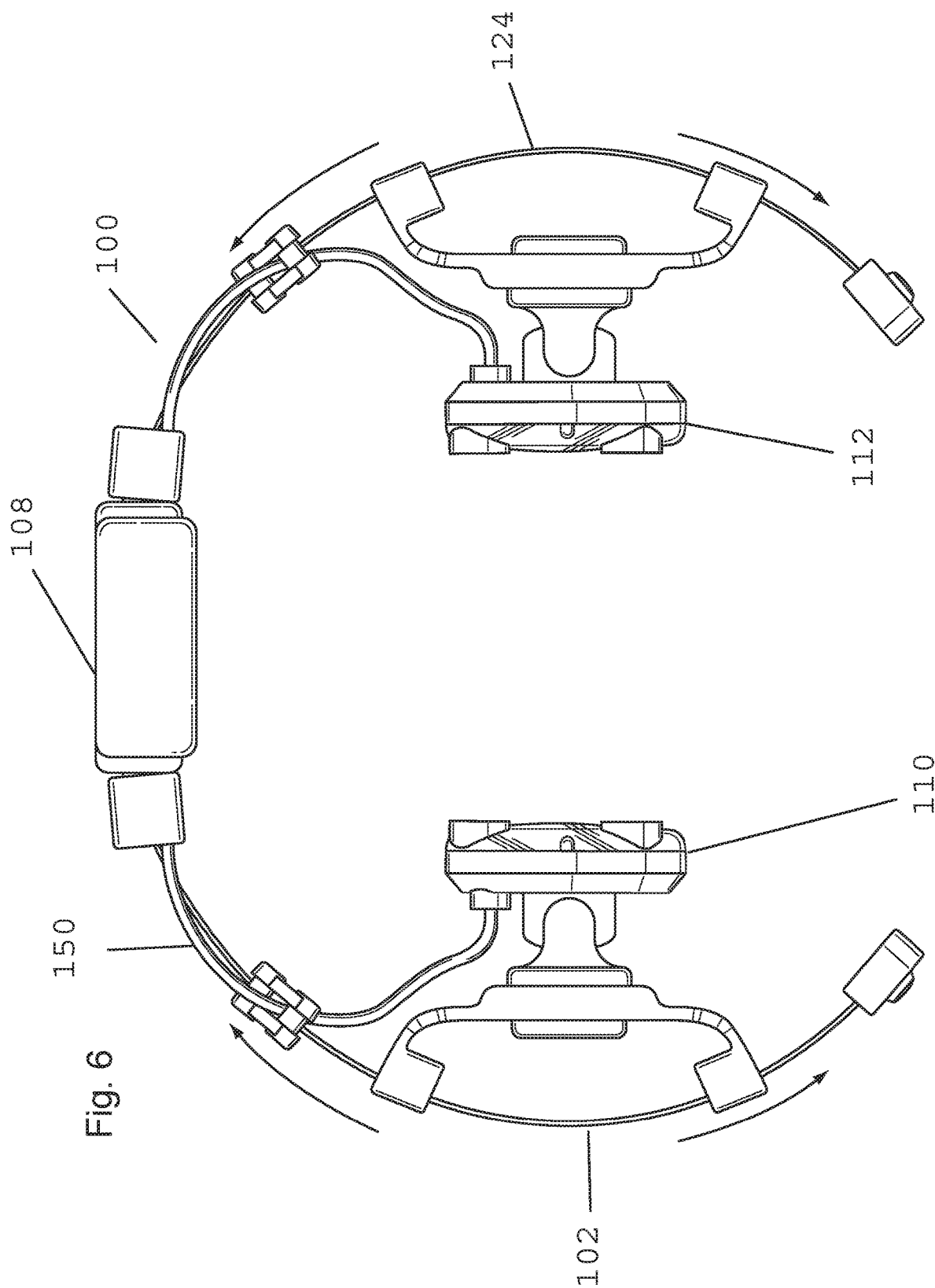
FIG. 6 illustrates a top view of a preferred embodiment of the apparatus of the present invention.

The light therapy unit 102 comprises one or more configured irradiation units 110, 112 which may be placed on the subject as shown in FIGS. 3 to 5. Each of the configured irradiation units 110, 112 includes a portable hollow casing having fixed dimensions, a sized internal spatial volume, and an external surface configuration suitable for application to the subject patient 200. The portable hollow casing comprises a light energy transmitting material which forms at least a portion of the configured external surface for said hollow casing. At least one light generating unit is entirely housed and contained within said internal spatial volume of said hollow casing and is capable of generating light energy sufficient to penetrate through the skin and to pass into the body. Each of the configured irradiation units 110, 112 also has a driver circuit which is in communication with the controller 108 and controls the light generating unit(s).

A frame 124 is provided in the light therapy unit 102 to support the configured irradiation units 110, 112 and to adapt the light therapy unit 102 for at will placement of the light transmitting external surface of the configured irradiation units 110, 112 at a fixed position and desired irradiation direction on the subject patient 200. Support pads are preferably provided to help secure the light therapy unit 102 to the subject patient 200 and making it more comfortable to wear.

Figure 12:
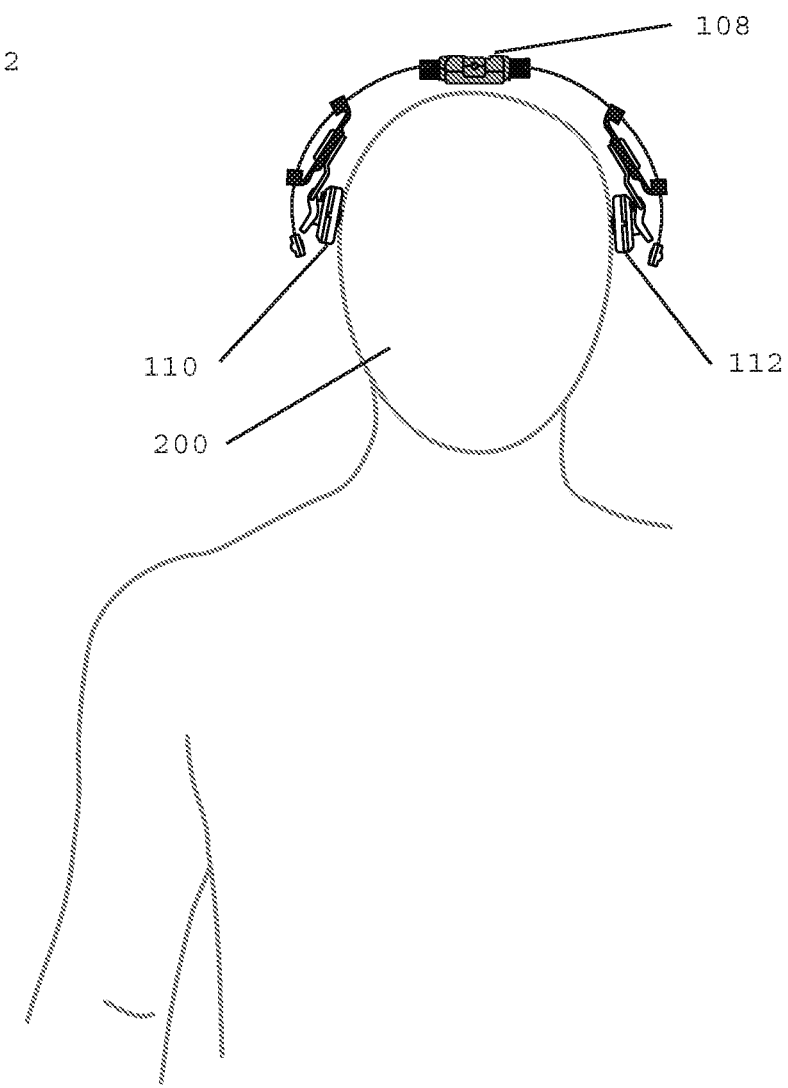
FIGS. 12 to 13 illustrate a preferred embodiment of the apparatus of the present invention when about to be applied to a head of a subject for Deep Brain Stimulation.
Figure 13:
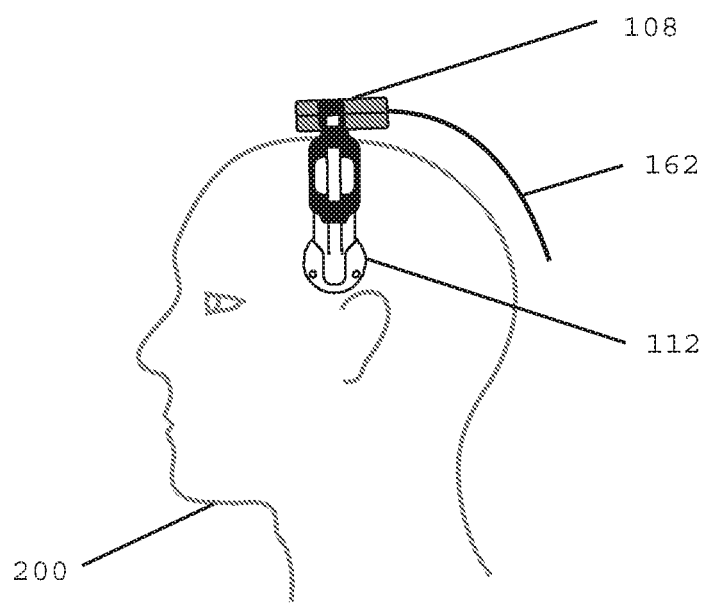

In the preferred embodiment shown in FIGS. 1 to 6, the frame 124 supports two configured irradiation units 110, 112 and each configured irradiation unit 110, 112 has at least one light generating unit(s) each. In the preferred embodiment shown in FIGS. 3 to 5, the units 110, 112 are positioned to target the vagus nerves on either side of the neck of the subject patient 200 for VNS. In the preferred embodiment shown in FIGS. 12 to 13, the units 110, 112 are positioned on the head of the subject patient 200 for DBS.

As can be seen in FIGS. 1 and 5, the intranasal unit 106 includes a nose clip 140. The nose clip 140 holds a configured irradiation lens 142 inside one of the nostrils of the subject. The configured irradiation lens 142 includes a portable hollow casing having fixed dimensions, a sized internal spatial volume, and an external surface configuration suitable for application to the interior of the nostrils. The portable casing comprises a light energy transmitting material which forms at least a portion of the configured external surface for said hollow casing. At least one light generating unit is entirely housed and contained within said internal spatial volume of said hollow casing and is capable of generating light energy sufficient to penetrate through the nasal tissues and to pass into the brain. The intranasal unit 106 targets areas of the ventral or underside of the brain such as the ventral medial prefrontal cortex (vmPFC), directly and indirectly via the olfactory bulb to the entorhinal cortex (EC) and parahippocampal area (including the hippocampus).

A first connector 150 is in electrical communication with the configured irradiation units 110, 112 of the light therapy unit 102, via the driver circuits. A second connector 154 is in electrical communication with the configured irradiation lens 142 of the intranasal unit 106. This allows for on-demand conveyance of direct electrical current from the controller 108 to the light generating units in the configured irradiation units 110, 112 of the light therapy unit 102 and the light generating unit(s) in configured irradiation lens 142 in the intranasal light therapy unit 106.

A portable power bank 160 provides electrical current to the apparatus 100. The power bank 160 can be a standard power bank comprising an encased battery with a circuit to control power flow. Preferably, the power bank 160 is rechargeable by plugging it into an electrical grid via a cable, such that the power bank 160 draws in and stores electrical energy. Alternatively, the power bank 160 may be recharged by other means, such as using photovoltaic panels which charge the internal battery with solar energy. A third connector 162 provides electrical communication between the power bank 160 and the controller 108. As such, the power bank 160 provides electrical current to the controller 108, which in turn provides electrical current to the light generating units of the apparatus 100.

In an alternative embodiment, a tablet computer provides a system interface for the apparatus 100. The tablet computer has downloaded thereon a PBM parameter-setting computer application which can: (i) turn the controller assembly on and off; and/or (ii) adjust the light energy parameters of each individual light generating unit, including but not limited to wavelength, coherency/synchrony, energy (as measured in Joules (J)), Power (as measured in Watts (W) or milliwatts (mW)), irradiance (W/cm$^2$), radiant exposure or dose or fluence density (J/cm$^2$), exposure time (seconds), wave type (continuous or pulse), duty cycle (percentage), fraction protocol (number of patient treatment sessions), light beam size (area of landed beam), and light beam penetration (delivery) distance. Preferably, each of the configured irradiation units 110, 112 and the configured irradiation lens 142 can be selectively switched on and off, as each has its own light generating unit and its own driver circuit. In further alternative embodiments, the tablet computer may be replaced by a smart phone, smart watch, laptop computer or desktop computer.

Furthermore, the tablet computer could serves as a system interface where a user selects icons on the touch screen to turn the controller 108 on and off and/or adjust the light energy parameters of each individual light generating unit. Once the user inputs instructions into the system interface, instructions are transmitted to the controller 108 which then adjusts the parameters of the light energy being delivered to by the light generating units. In a preferred embodiment, the tablet computer is linked to and communicates with the controller 108 by wireless means. However, any appropriate wired or wireless communications via protocols such as BLUETOOTH™, Wi-Fi, Near Field Communications (NFC), Radio Frequency Identification (RFID), 3G, Long Term Evolution (LTE), Universal Serial Bus (USB) and other protocols and technologies known to those skilled in the art can be used to link the tablet computer to the controller 108.

Experimental Section

1. Vagus Nerve Stimulation

The quality of vagus nerve function can be represented by the vagus tone. A good vagus tone reflects a balanced autonomic nervous system (ANS), encompassing a good parasympathetic nervous system. Apart from other health outcomes, it is desirable for stress reduction, reduction of inflammation and a variety of compromised conditions. Experiments using VNS in accordance with a preferred embodiment of the invention were conducted to test whether it was helpful is achieving a balanced ANS.

The various measurable metrics used to test the invention relevant to achieving a balanced ANS include the following:

Diagnosis of the interaction between the heart rate and breathing, breathing being detected from echocardiogram (ECG) data, which has been referred as the "Cardiac Brody Effect".

Heart rate variability (HRV) which is a measure of the variation in time between each heartbeat, reflecting the ANS balance.

Respiratory Sinus Arrythmia (RSA) has been considered a better measurement of vagal tone than HRV. According the Polyvagal Theory, the RSA is an index of emotional regulation, relating to the ANS.

Also useful is a method to detect and diagnose the periodicity of heart rate increases and decreases in relation to each inhale and exhale from hand-to-hand ECG, called the Respiratory Sinus Arrythmia Synchronization (RSAsync). Here it is expressed as an index between 0-100 where 100 is indicating a very well-functioning Respiratory-Cardiac oxygen vagal synchronization.

The quality of the vagus tone can be measured with the following metrics:

Heart rate (within normal range of 60 to 100 beats per minute)

Heart rate variability (HRV)

Breathing sequence

Respiratory sinus arrythmia (RSA)

RSA Synchronization (RSAsync)

Vagal Homeostasis Index (VHI)

Summary—Heart and breathing rhythm synchronization (H/B)

Methodology

Two subjects were tested—a 64-year old male and a 65-year old female, both of good health. Both subjects were given VNS using a preferred apparatus of the present invention.

Two pulse frequencies were tested— 20 Hz and 10 Hz. A series of measurements and under various conditions are shown below. The apparatus was tested on the male and female subjects once daily, switching between 20 Hz and 10 Hz.

Measurements of the above-mentioned metrics were taken using a wearable device from Vagus.co.

Results from VNS Treatment Using Pulse Frequency of 20 Hz

Day 1 (Male)

|  | Pre | Post 10 Hz 20 minutes |
|---|---|---|
| Summary - H/B sync | Very low | Good |
| Pulse | 72 | 65 |
| HRV | 19 | 32 |
| Breathing | 67 | 37 |
| RSA | 0 | 93 |
| RSA Sync | 100 | 75 |
| VHI | 50 | 84 |

Comments:

Intervention and measurements under normal living conditions

Day 2 (Female)

|  | Pre | Post 10 Hz 20 minutes |
|---|---|---|
| Summary - H/B sync | Good | Good |
| Pulse | 63 | 61 |
| HRV | 37 | 35 |
| Breathing | 27 | 28 |
| RSA | 86 | 87 |
| RSA Sync | 75 | 79 |
| VHI | 81 | 83 |

Comments:

Intervention and measurement under normal daily living environment

Day 3 (Male)

|  | Pre | Post 20 Hz 20 minutes |
|---|---|---|
| Summary - H/B sync | Good | Very Good |
| Pulse | 72 | 69 |
| HRV | 36 | 42 |
| Breathing | 34 | 37 |
| RSA | 93 | 83 |
| RSA Sync | 75 | 84 |
| VHI | 84 | 83 |

Comments:

Treatment and measurements after meditation

Day 4 (Female)

|  | Post 10 min meditation only | Post 20 Hz 10 min LED on ganglion | Post 20 Hz 10 min LED on vagus nerves | Repeat measures after 1 minute |
|---|---|---|---|---|
| Summary - H/B sync | Good | Average | Very good | Very good |
| Pulse | 65 | 62 | 60 | 63 |
| HRV | 40 | 42 | 34 | 33 |
| Breathing | 71 | 43 | 37 | 100 |
| RSA | 85 | 61 | 87 | 88 |
| RSA Sync | 76 | 68 | 80 | 82 |
| VHI | 81 | 65 | 84 | 85 |

Comment:

Measured after meditation, the outcome from positioning on the ganglion was not as significant as positioning on the neck.

Day 5 (Male)

|  | Baseline, after normal daily work routine | Post 10 min meditation | Post 10 min meditation + 20 Hz on vagus nerves | Post another 10 min meditation + 20 Hz on vagus nerves | After 1 hour of routine work post-stimulation |
|---|---|---|---|---|---|
| Summary - H/B sync | Low | Good | Very good | Very good | Good |
| Pulse | 71 | 70 | 69 | 67 | 65 |
| HRV | 48 | 37 | 33 | 35 | 36 |
| Breathing | 35 | 47 | 42 | 36 | 38 |
| RSA | 49 | 89 | 93 | 85 | 87 |
| RSA Sync | 51 | 74 | 81 | 83 | 74 |
| VHI | 50 | 82 | 87 | 84 | 80 |

Comment:

Vagus nerve stimulation improves the outcomes beyond what is achievable from meditation. The benefit recedes one hour after stopping treatment Results from VNS Treatment Using Pulse Frequency of 10 Hz Day 1 (Female)

|  | Pre | Post 10 Hz 20 minutes |
|---|---|---|
| Summary - H/B sync | Average | V. Low |
| Pulse | 72 | 89 |
| HRV | 37 | 163 |
| Breathing | 41 | 73 |
| RSA | 94 | 2 |
| RSA Sync | 59 | 92 |
| VHI | 76 | 47 |

Comments:

Testing with some stress. The significant drop in vagal tone, post stimulation is unexplained.

Day 2 (Male)

|  | Pre | Post 10 Hz 20 minutes |
|---|---|---|
| Summary - H/B sync | Good | V. Good |
| Pulse | 61 | 63 |
| HRV | 35 | 49 |
| Breathing | 28 | 32 |
| RSA | 87 | 92 |
| RSA Sync | 79 | 86 |
| VHI | 83 | 89 |

Comments:

Treatment and measures under normal daily living environment

Day 3 (Female)

|  | Pre | Post 10 Hz 20 minutes |
|---|---|---|
| Summary - H/B sync | Average | Very Good |
| Pulse | 67 | 65 |
| HRV | 55 | 38 |
| Breathing | 45 | 49 |
| RSA | 85 | 96 |
| RSA Sync | 66 | 86 |
| VHI | 76 | 91 |

Comments:

Treatment and measures under normal daily living environment

FIGS. 7 to 11 are graphs of the H/B sync, and show how well the autonomic nervous system is in balance—the closer the two lines are to each other, the more optimum.

Figure 7:
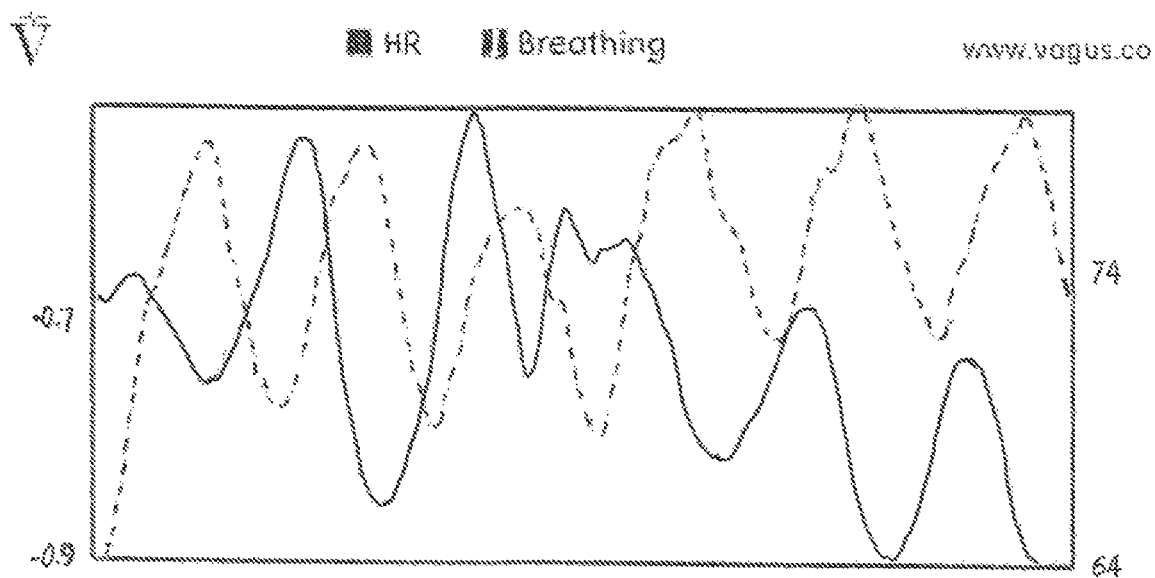
FIGS. 7 to 11 are graphs showing the results of VNS experiments conducted on a subject using the apparatus of the present invention, and in particular, show the heart and breathing rhythm synchronization (H/B sync) under the following scenarios: (i) Baseline, after normal daily work routine (FIG. 7); (ii) Post 10 min meditation (FIG. 8); (iii) Post 10 min meditation+20 Hz on vagus nerves (FIG. 9); (iv) Post another 10 min meditation+20 Hz on vagus nerves (FIG. 10); and (v) After 1 further hour of routine work post-stimulation (FIG. 11)
Figure 8:
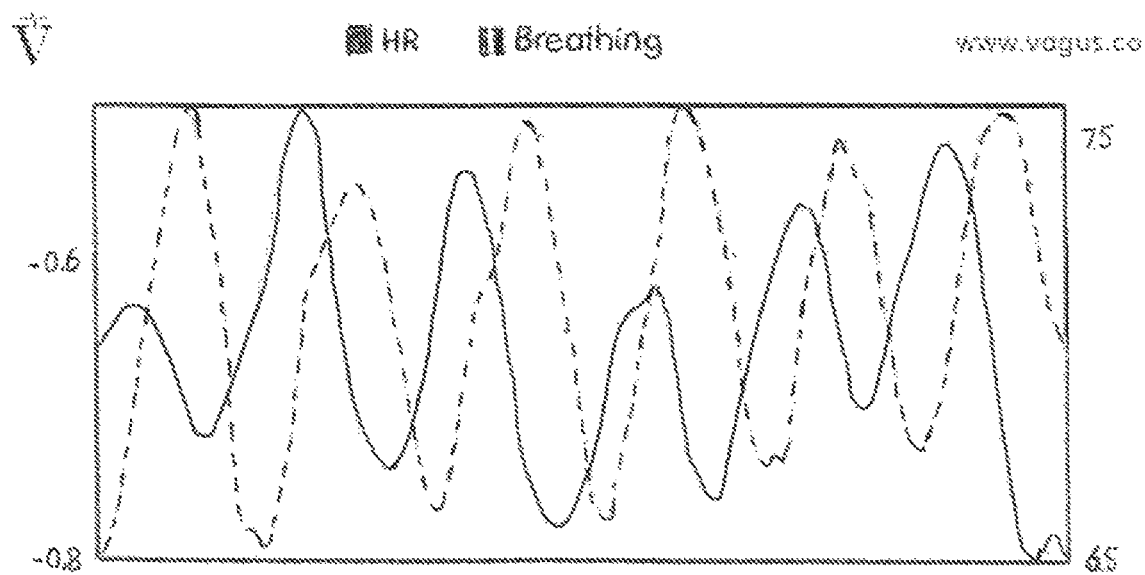
Figure 9:
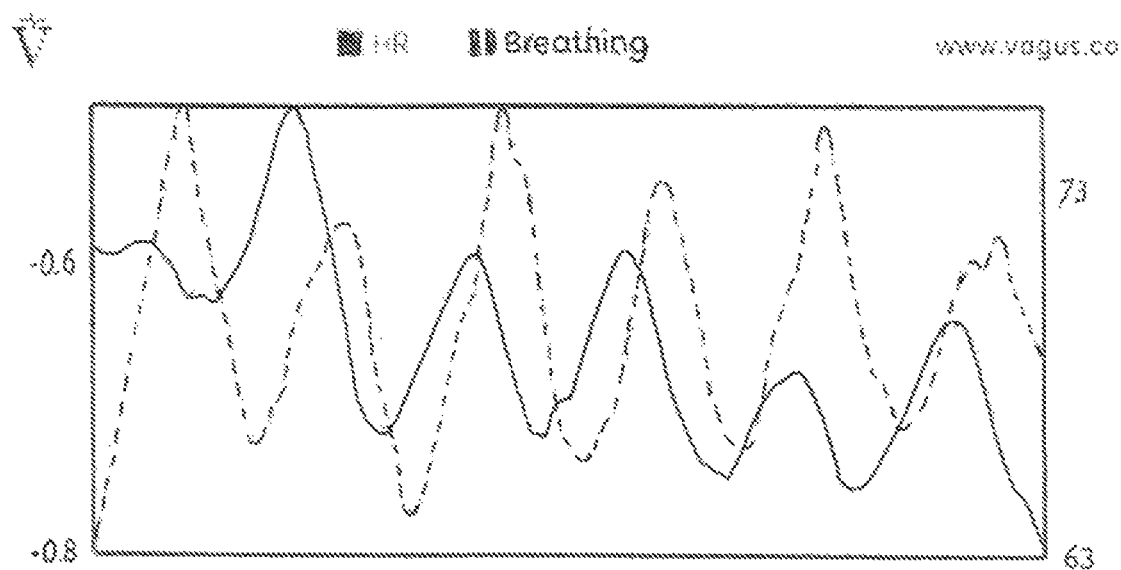
Figure 10:
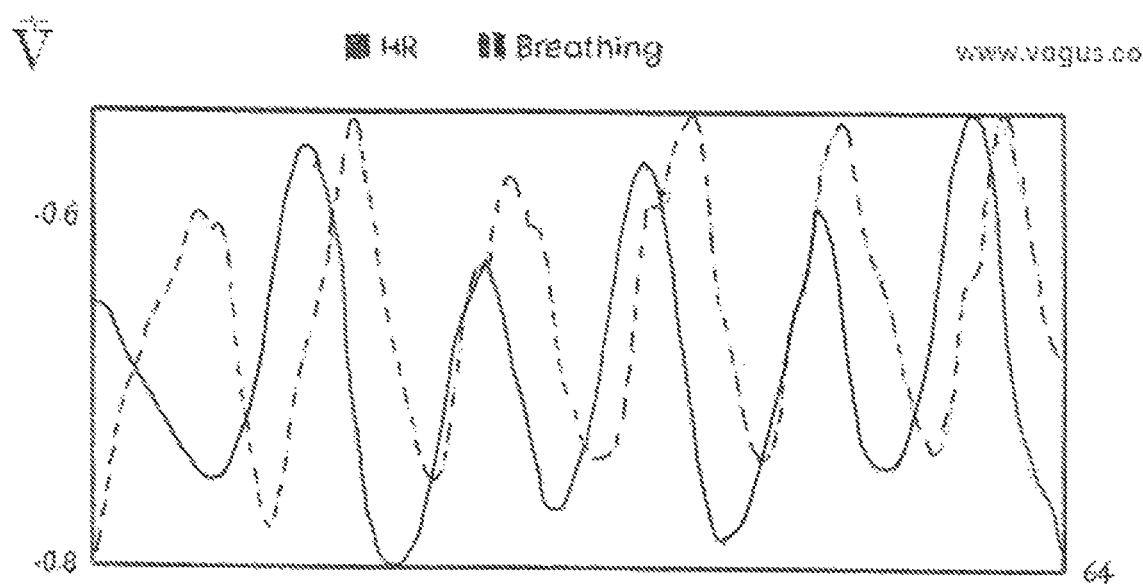
Figure 11:
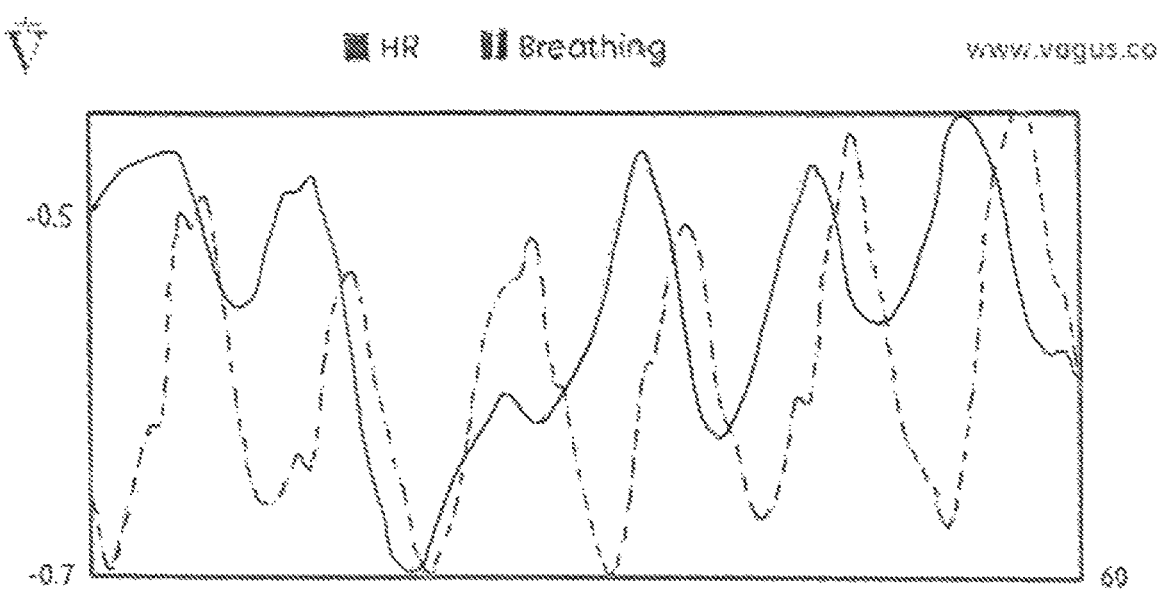

The figures represent the data collected on Day 5 for the Male subject, testing the preferred embodiment of the invention pulsing at 20 Hz under the following scenarios:
 (i) Baseline, after normal daily work routine (FIG. 7);
 (ii) Post 10 min meditation (FIG. 8);
 (iii) Post 10 min meditation+20 Hz on vagus nerves (FIG. 9);
 (iv) Post another 10 min meditation+20 Hz on vagus nerves (FIG. 10); and
 (v) After 1 further hour of routine work post-stimulation (FIG. 11).

Conclusions

The invention can produce significant restoration of the autonomic nervous system, improving the quality of the parasympathetic nervous system which is identified as the vagus tone.

The effects are measurable

From the tests, the pulse frequency of 20 Hz is more reliable than 10 Hz, suggesting that pulse frequencies matter. This also suggests that other effects can be individualized for desired effects.

2. Deep Brain Stimulation

A preferred apparatus of the present invention was tested on three different subjects with Parkinson's Disease on separate days:

Subject A: 35-year old male with early onset PD, presenting mild tremors.

Subject B: 55-year old male diagnosed with PD, with some impairment in movement and had difficulty speaking clearly.

Subject C: 66-year old male who was a family physician and was wheelchair bound. He had advanced stage PD, presenting severe uncontrolled movements (dyskinesia) in the hands and legs.

Methodology

A neurologist was present during the testing and helped to make observations on the subject patients.

The subjects were each asked to confirm that they have been diagnosed with PD with movement disorder. They were then asked to describe their prevailing symptoms.

Each of them was asked to sit on a chair in a relaxed posture and close their eyes while treated with the preferred apparatus of the present invention.

The preferred apparatus was set to direct light energy at a wavelength of 810 nm and power delivery of 50 mW/cm$^2$ in continuous wave.

The light emitting diode (LED) of the preferred apparatus was positioned on the temporal lobe on the T3/T4 positions according to the 10-20 EEG system. In this position, the preferred apparatus directed light energy towards the globus pallidus internus (GPi) and subthalamic nucleus (STN)

This treatment was carried out over 20 minutes, after which qualitative data was collected as follows:
 (i) The subjects were observed for any change in symptoms, primarily in the severity of visually apparent uncontrolled movements and behavior such as the quality of conversation.
 (ii) The subjects were also asked about changes in the relevant symptoms immediately after the intervention and 30 minutes after.

Results

Subject A: The subject reported that his tremors were reduced noticeably after a single session and remained so after a further 30 minutes.

Subject B: It was apparent that the subject spoke more clearly after the 20-minute treatment session. The subject reported that he felt an improvement in his speech and movement.

Subject C: The reduction in involuntary movement in the hands and legs was clear, and the subject was able to walk for a short distance unaided. Thirty minutes later, he largely maintained the improvement. The subject who was a physician, self-diagnosed to have experienced at least a temporary improvement in his symptoms.

No side effects were observed or reported by any of the subject patients.

Conclusions

The evidence here suggests that the present invention has the potential as a noninvasive way to help treat movement disorder diseases such as Parkinson's Disease.

The scope of the claims should not be limited by the preferred embodiments set forth in the examples, but should be given the broadest interpretation consistent with the description as a whole.

The invention claimed is:

1. A self-administrable apparatus for performing non-invasive neurostimulation therapy of a living mammalian subject on-demand, said self-administrable apparatus comprising:
 one or more configured irradiation units comprising a portable hollow casing having fixed dimensions, a sized internal spatial volume and an external surface configuration suitable for application to a body, said portable hollow casing of each configured irradiation unit being comprised of:
  (i) a light energy transmitting material which forms at least a portion of the configured external surface for said hollow casing of each configured irradiation unit; and
  (ii) at least one light generating unit housed and contained within said sized internal spatial volume of said hollow casing of each configured irradiation unit and which is capable of generating light energy of at least one preselected wavelength selected from a group consisting of near infrared light wavelengths and visible red light wavelengths, at a predetermined energy intensity and for a preset time duration on-demand sufficient to penetrate through skin and to pass into an interior part of the body,
 whereby said one or more configured irradiation units can emit the light energy after application to the body and achieve passage of said emitted light energy through skin into an interior part of the body in-vivo;
 a frame adapted for support of said one or more configured irradiation units and for at-will placement of said light energy transmitting material of the external surface of said one or more configured irradiation units at a fixed position and desired irradiation direction;
 a controller assembly able to control on-demand delivery of the light energy from said one or more configured irradiation units into an interior part of the body in-vivo, said controller assembly including:

(a) a power source of on-demand direct electrical current,
(b) a central processing unit for controlling and directing the flow of such direct electrical current,
(c) at least one connector in electrical communication with the power source for on-demand conveyance of the direct electrical current to the central processing unit, and
(d) at least one connector in electrical communication with the one or more configured irradiation units for on-demand conveyance of the direct electrical current from said central processing unit to said at least one light generating unit;
wherein the frame is configured to position at least one of said configured irradiation units on a side of the neck of the subject to non-invasively stimulate a vagus nerve in the neck of the subject with the light energy.

2. The apparatus of claim 1, further comprising:
a configured intranasal irradiation lens comprising:
a second portable hollow casing having fixed dimensions, a second sized internal spatial volume, and a second external surface configuration suitable for in-vivo insertion into a nasal cavity space of a nostril without causing substantial impairment to an ability of the subject to breathe and without invading nasal tissues of the subject, said second portable hollow casing being comprised of a second light energy transmitting material which forms at least a portion of the second external surface configuration of said second portable hollow casing; and
at least one intranasal light generating unit housed and contained within said second sized internal spatial volume of said second portable hollow casing and which is capable of generating light energy sufficient to penetrate through the nasal tissues and to pass into a brain,
whereby said configured intranasal irradiation lens emits the light energy in any desired direction within the nasal cavity after in-vivo insertion and achieves passage of said emitted light energy from the nasal cavity into at least one portion of the brain in-vivo; and
a self-administrable applicator means adapted for support of said configured intranasal irradiation lens and for at will placement of said second light energy transmitting external surface of said second portable hollow casing of said configured intranasal irradiation lens at a fixed position and desired irradiation direction within the nostril adjacent to an internal lining of the nasal cavity of the subject.

3. The apparatus of claim 1, wherein said controller assembly directs the light energy to have a wavelength of about 600 nm to 1500 nm.

4. The apparatus of claim 1, wherein said controller assembly directs the light energy to be pulsed at a frequency of about 10 Hz to 100 Hz.

5. The apparatus of claim 1, wherein said controller assembly directs the light energy to have a light energy density in the range of about 5 to 1800 J/cm$^2$.

6. The apparatus of claim 1, wherein said controller assembly regulates a patient exposure time for each therapeutic treatment session to about 1 minute to 1 hour in duration.

7. The apparatus of claim 1, wherein said apparatus is for the treatment of a neurological condition.

8. The apparatus of claim 1, wherein said at least one light generating unit is a light emitting diode (LED).

9. A self-administrable method for performing non-invasive neurostimulation therapy of a living mammalian subject on-demand, said self-administrable method comprising the steps of:
(A) obtaining a light energy-emitting apparatus comprised of:
one or more configured irradiation units comprising a portable hollow casing having fixed dimensions, a sized internal spatial volume and an external surface configuration suitable for application to a body, said portable hollow casing of each configured irradiation unit being comprised of:
(i) a light energy transmitting material which forms at least a portion of the configured external surface for said hollow casing of each configured irradiation unit; and
(ii) at least one light generating unit housed and contained within said sized internal spatial volume of said hollow casing of each configured irradiation unit and which is capable of generating light energy of at least one preselected wavelength selected from a group consisting of near infrared light wavelengths and visible red light wavelengths, at a predetermined energy intensity and for a preset time duration on-demand sufficient to penetrate through skin and to pass into an interior part of the body,
whereby said one or more configured irradiation units can emit the light energy after application to the body and achieve passage of said emitted light energy through skin into an interior part of the body in-vivo;
a frame adapted for support of said one or more configured irradiation units and for at-will placement of said light energy transmitting external material of the external surface of said one or more configured irradiation units at a fixed position and desired irradiation direction;
a controller assembly able to control on-demand delivery of light energy from said one or more configured irradiation units into an interior part of the body in-vivo, said controller assembly including:
(a) a power source of on-demand direct electrical current,
(b) a central processing unit for controlling and directing the flow of such direct electrical current,
(c) at least one connector in electrical communication with the power source for on-demand conveyance of the direct electrical current to the central processing unit, and
(d) at least one connector in electrical communication with the one or more configured irradiation units for on-demand conveyance of the direct electrical current from said central processing unit to said at least one light generating unit;
(B) causing said at least one light generating unit of said one or more configured irradiation units to generate the light energy of at least one preselected wavelength selected from the group consisting of near infrared light wavelengths and visible red light wavelengths, at a predetermined energy intensity and for a preset time duration on-demand sufficient to penetrate through the subject's skin and to pass into the interior of the subject's body;
wherein the frame positions at least one of said configured irradiation units on a side of the neck of the subject to direct the light energy to a vagus nerve in the neck of the subject; and (C) non-invasively stimulating the vagus nerve in the neck of the subject with the light energy.

10. The method of claim 9, wherein the apparatus further comprises:
a configured intranasal irradiation lens comprising:
a second portable hollow casing having fixed dimensions, a second sized internal spatial volume, and a second external surface configuration suitable for in-vivo insertion into a nasal cavity space of a nostril without causing substantial impairment to an ability of the subject to breathe and without invading nasal tissues of the subject, said second portable hollow casing being comprised of a second light energy transmitting material which forms at least a portion of the second external surface configuration of said second portable hollow casing; and
at least one intranasal light generating unit housed and contained within said second sized internal spatial volume of said second portable hollow casing and which is capable of generating light energy sufficient to penetrate through the nasal tissues and to pass into the brain,
whereby said configured intranasal irradiation lens emits the light energy in any desired direction within the nasal cavity after in-vivo insertion and achieve passage of said emitted light energy from the nasal cavity into at least one portion of the brain in-vivo; and
a self-administrable applicator means adapted for support of said configured intranasal irradiation lens and for at will placement of said second light energy transmitting external surface of said second portable hollow casing of said configured intranasal irradiation lens at a fixed position and desired irradiation direction within the nostril adjacent to an internal lining of the nasal cavity of the subject.

11. The method of claim 9, wherein said controller assembly directs the light energy to have a wavelength of about 600 nm to 1500 nm.

12. The method of claim 9, wherein said controller assembly directs the light energy to be pulsed at a frequency of about 10 Hz to 100 Hz.

13. The method of claim 9, wherein said controller assembly directs the light energy to have a light energy density in the range of about 5 to 1800 J/cm$^2$.

14. The method of claim 9, wherein said controller assembly regulates a patient exposure time for each therapeutic treatment session to about 1 minute to 1 hour in duration.

15. The method of claim 9, wherein said method is for the treatment of a neurological condition.

16. The method of claim 9, wherein said at least one light generating unit is a light emitting diode (LED).

* * * * *